US011439871B2

(12) United States Patent
Liu et al.

(10) Patent No.: US 11,439,871 B2
(45) Date of Patent: Sep. 13, 2022

(54) SYSTEM AND METHOD FOR REHABILITATION

(71) Applicant: Conzian Ltd., Taipei (TW)

(72) Inventors: Yan-Fu Liu, Taipei (TW); Po-Jui Huang, Taipei (TW); Liang-Kai Wang, Taipei (TW); Chung-Hsien Wu, Taipei (TW); Jian-Lin Chen, Taipei (TW)

(73) Assignee: Conzian Ltd., Taipei (TW)

( * ) Notice: Subject to any disclaimer, the term of this patent is extended or adjusted under 35 U.S.C. 154(b) by 773 days.

(21) Appl. No.: 16/286,670

(22) Filed: Feb. 27, 2019

(65) Prior Publication Data

US 2020/0269091 A1 Aug. 27, 2020

(51) Int. Cl.
*G16H 20/30* (2018.01)
*A63B 24/00* (2006.01)
*A63B 71/06* (2006.01)

(52) U.S. Cl.
CPC ...... *A63B 24/0087* (2013.01); *A63B 24/0075* (2013.01); *A63B 71/0619* (2013.01);
(Continued)

(58) Field of Classification Search
CPC ............ A63B 24/0006; A63B 24/0062; A63B 24/0075; A63B 24/0087; A63B 71/0619; A63B 71/0622; A63B 2220/17; A63B 2220/51; A63B 2220/58; A63B 2220/80; A63B 2220/803; A63B 2220/806; A63B 2225/20; A63B 2225/50; A63B 2024/0009; A63B 2024/0015; A63B 2071/065; A63B 2071/0677; G16H 20/30; A61B 2505/09; A61H 2201/165; A61H 2201/5007;
(Continued)

(56) References Cited

U.S. PATENT DOCUMENTS 9,069,381 B2   6/2015   Geisner et al.
10,065,074 B1*  9/2018   Hoang ................. G09B 19/003
(Continued)

FOREIGN PATENT DOCUMENTS

CN   104871163 B   11/2018
TW   200906377 A   2/2009
(Continued)

*Primary Examiner* — Jay Trent Liddle
*Assistant Examiner* — Alyssa N Brandley
(74) *Attorney, Agent, or Firm* — ScienBiziP, P.C.

(57) ABSTRACT

A system for determining an assessment of at least one exercise performed by a user is described. The system includes an input device, and a computing device. The input device is configured to monitor at least one exercise performed by a user. The computing device includes processors and a memory. The memory is coupled to the processors and stores program instructions that when executed by the processors cause the processors to: (1) generate a user interface displaying a content; (2) provide an instruction associated with the at least one exercise; (3) determine an indication of movement associated with the at least one exercise; (4) in response to a determination of the indication of movement, determine an assessment of the at least one exercise; and (5) in response to a determination of the assessment of the at least one exercise, perform an operation.

18 Claims, 21 Drawing Sheets

(52) U.S. Cl.
CPC .......... *G16H 20/30* (2018.01); *A61B 2505/09* (2013.01); *A61H 2201/5007* (2013.01); *A63B 2220/17* (2013.01); *A63B 2220/51* (2013.01); *A63B 2220/58* (2013.01); *A63B 2225/20* (2013.01); *A63B 2225/50* (2013.01)

(58) Field of Classification Search
CPC .... A61H 2201/5058; A61H 2201/5061; A61H 2201/5064
See application file for complete search history.

(56) References Cited

U.S. PATENT DOCUMENTS

| | | | | |
|---|---|---|---|---|
| 2005/0079905 | A1* | 4/2005 | Martens | A63B 24/0087 463/1 |
| 2012/0277891 | A1* | 11/2012 | Aragones | G09B 19/003 700/91 |
| 2013/0196822 | A1* | 8/2013 | Watterson | A63B 24/0087 482/9 |
| 2015/0335950 | A1* | 11/2015 | Eder | A63B 21/4035 482/8 |
| 2017/0329933 | A1* | 11/2017 | Brust | G06F 16/24575 |

FOREIGN PATENT DOCUMENTS

| | | |
|---|---|---|
| TW | 201417796 A | 5/2014 |
| WO | WO-2017058913 A1 * | 9/2016 |
| WO | WO-2018024908 A1 * | 8/2017 |

\* cited by examiner

SYSTEM AND METHOD FOR REHABILITATION

FIELD

The present disclosure relates to a therapeutic system and more specifically to a rehabilitation system for monitoring an exercise performed by a user.

BACKGROUND

Physical therapy assists patients in recovering strength and movement. Typically, the patients have to repeat the exercises assigned by their healthcare providers at home. However, excising in absence of the healthcare providers increases the chance of incorrect movements, which reduces effectiveness of the exercises and potentially causes harm to the patients.

Furthermore, healthcare providers typically evaluate the outcome of the exercises only by examining the physical conditions of the patients during clinic visits. Such physical examination is inefficient for rehabilitation of the patient.

SUMMARY OF THE DISCLOSURE

The following presents a summary of examples of the present disclosure in order to provide a basic understanding of at least some of its examples. This summary is not an extensive overview of the present disclosure. It is not intended to identify key or critical elements of the present disclosure or to delineate the scope of the present disclosure. The following summary merely presents some concepts of the present disclosure in a general form as a prelude to the more detailed description provided below.

In one example, a system includes an input device, and a computing device. The input device is configured to monitor at least one exercise performed by a user. The computing device includes one or more processors and a memory. The memory is coupled to the one or more processors and stores program instructions that when executed by the one or more processors cause the one or more processors to: generate a user interface displaying a content; provide an instruction associated with the at least one exercise; determine an indication of movement associated with the at least one exercise; in response to a determination of the indication of movement, determine an assessment of the at least one exercise; and in response to a determination of the assessment of the at least one exercise, perform an operation.

In another example a therapeutic system includes a wearable device and a computing device. The wearable device has an input device configured to monitor at least one exercise performed by a user. The computing device includes one or more processors and a memory. The memory is coupled to the one or more processors and stores program instructions that when executed by the one or more processors cause the one or more processors to at least: provide a rehabilitation routine including the at least one exercise; determine an indication of movement associated with the at least one exercise; in response to a determination of the indication of movement, provide a real-time evaluation of the at least one exercise; and in response to a determination of the real-time evaluation of the at least one exercise, perform an operation.

In the other example, a method is for determining an assessment of at least one exercise performed by a user. The method includes the steps of: monitoring the at least one exercise by an input device affixed to a wearable equipment on the user; generating a user interface displaying a content by a computing device; providing an instruction associated with the at least one exercise by the computing device; and determining an indication of movement associated with the at least one exercise by the computing device.

The details of one or more examples are set forth in the accompanying drawings and description below.

BRIEF DESCRIPTION OF THE DRAWINGS

The accompanying drawings illustrate one or more embodiments of the present disclosure and, together with the written description, explain the principles of the present disclosure. Wherever possible, the same reference numbers are used throughout the drawings referring to the same or like elements of an embodiment.

DETAILED DESCRIPTION

Figure 1:
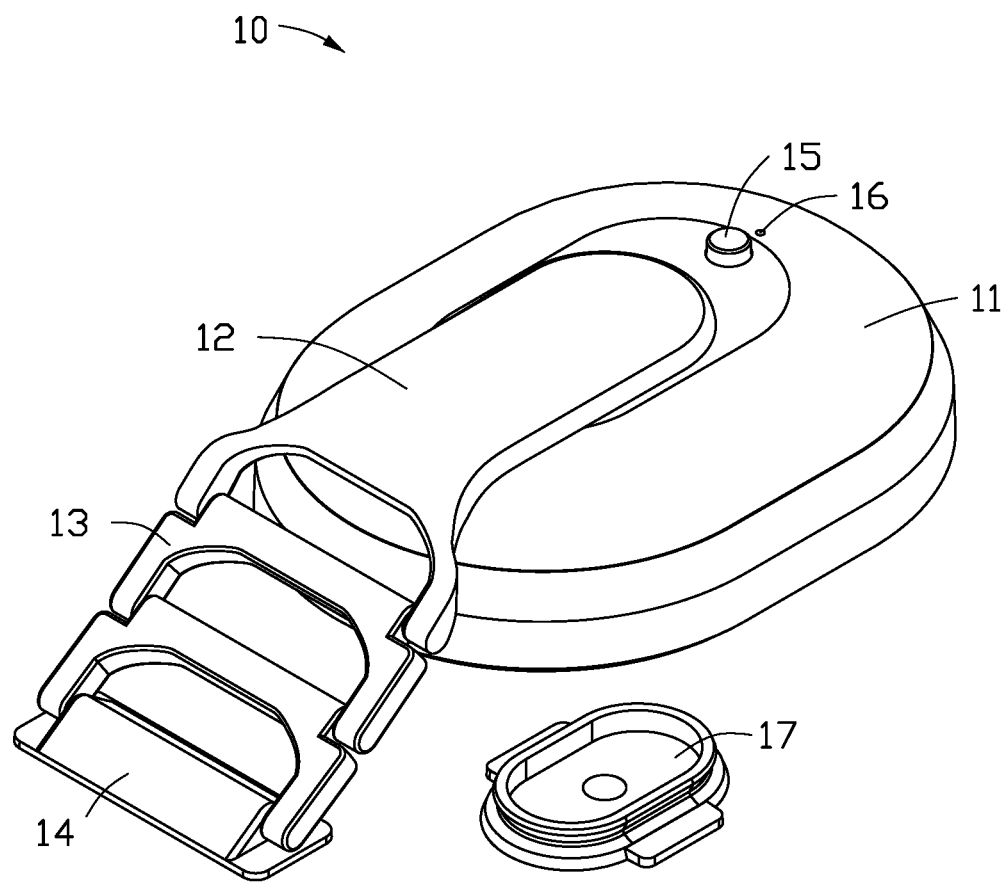
FIG. 1 is a perspective view of a monitoring device assembly in accordance with an embodiment of the present disclosure.

To facilitate an understanding of the principles and features of the various embodiments of the present disclosure, various illustrative embodiments are explained below. Although exemplary embodiments of the present disclosure are explained in detail, it is to be understood that other embodiments are contemplated. Accordingly, it is not intended that the present disclosure is limited in its scope to the details of construction and arrangement of components set forth in the following description or illustrated in the drawings. The present disclosure is capable of other embodiments and of being practiced or carried out in various ways.

FIG. 1 illustrates a perspective view of a monitoring device assembly 10 in accordance with an embodiment of the present disclosure. The monitoring device assembly 10 includes a device body 11, a shaft 12, a hinge 13, a hinge base 14, a power button 15, an indication light 16, and a bottom fixture 17. The device body 11 has a sensor chip (not shown). In some embodiments, a camera (not shown) may be placed on the device body 11 and coupled to the sensor chip. In certain embodiments, an external camera (not shown) may be used and wirelessly connected to the sensor chip.

One end of the shaft 12 is connected to the device body 11, and the other end of the shaft 12 is connected to the hinge 13. The shaft 12 is rotatable with respect to the device body 11. The hinge 13 is connected to the hinge base 14. The device body 11 has a bottom opening (not shown) for accommodating the bottom fixture 17.

Figure 2A:
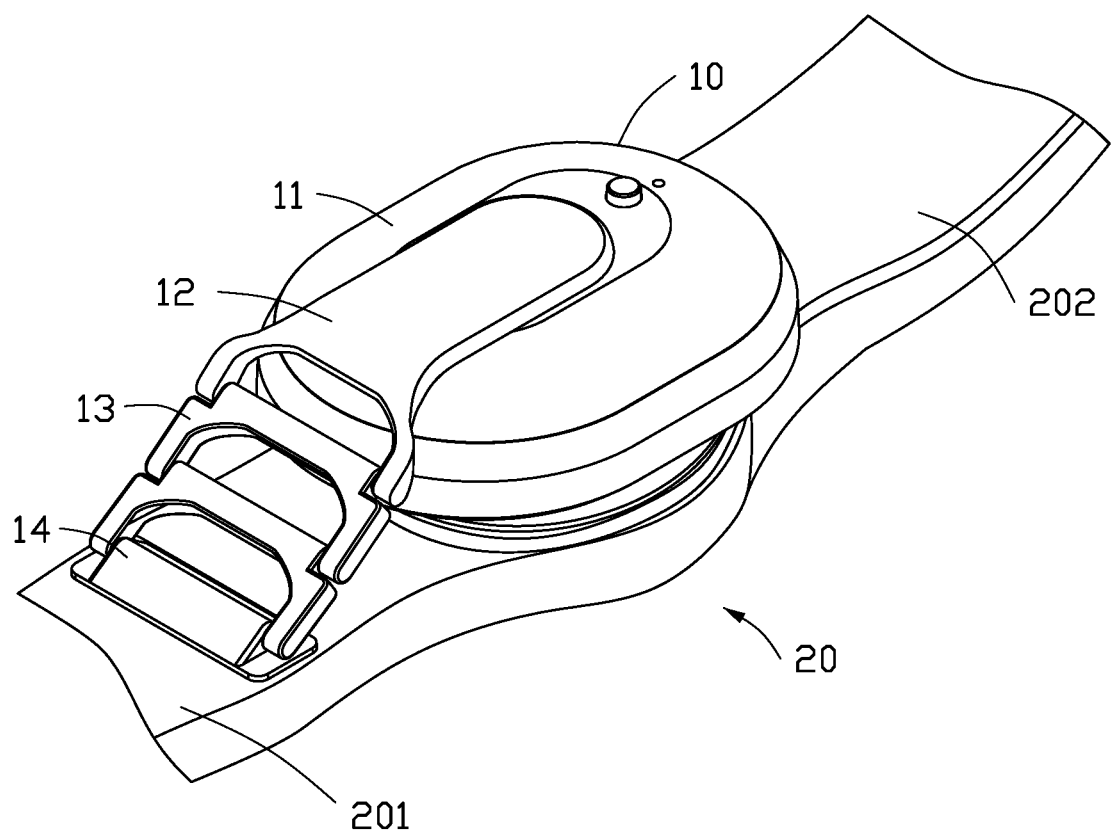
FIG. 2A is a perspective view of the monitoring device assembly attached to an external equipment in accordance with an embodiment of the present disclosure.

FIG. 2A illustrates a perspective view of the monitoring device assembly 10 attached to an external equipment 20 in accordance with an embodiment of the present disclosure. As partially shown in FIG. 2A, the external equipment 20 includes a first member 201 and a second member 202. The first member 201 and the second member 202 are rotatably joined. The hinge base 14 may be fixedly attached to the first member 201, and the bottom fixture 17 (not shown) may be fixedly attached to the second member 202. As illustrated in FIG. 2A, lateral movement of the shaft 12 is constrained by the hinge 13; therefore, when the first member 201 and the second member 202 move (e.g., rotate) with respect to each other, the measurement between the shaft 12 and the device body 11 corresponds to the movement between the first member 201 and the second member 202.

Figure 2B:
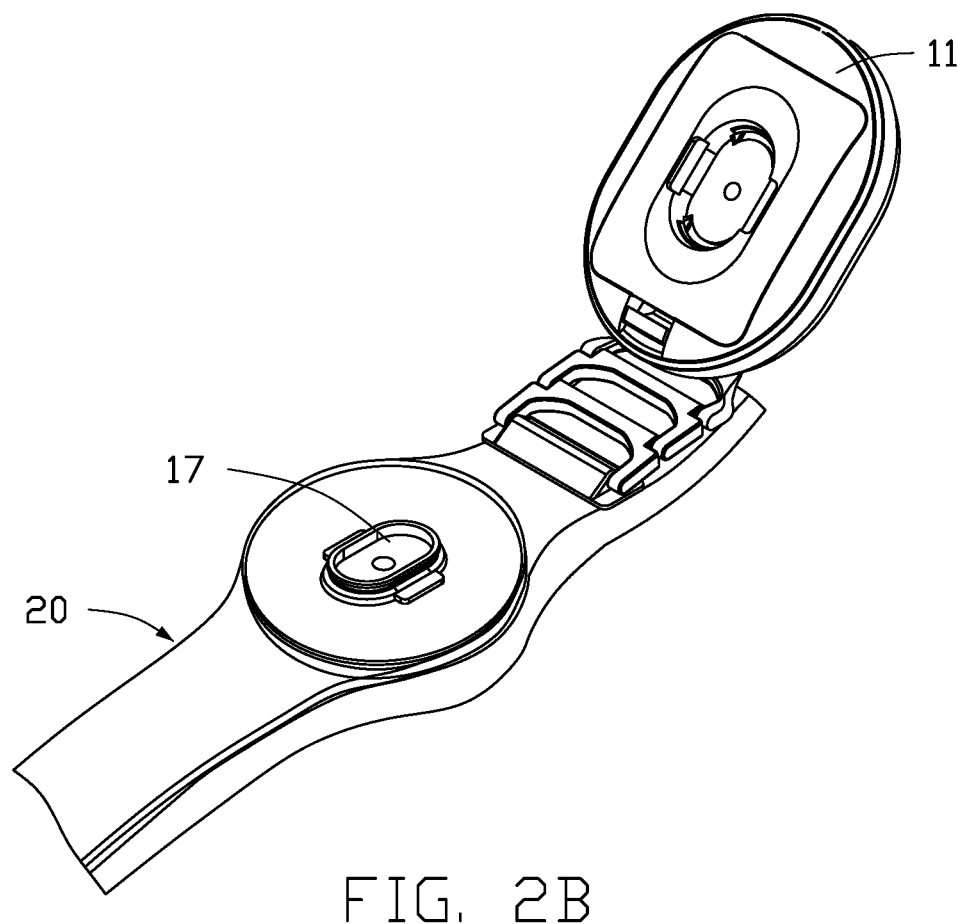
FIGS. 2B-2C are perspective views respectively showing a device body of the monitoring device assembly being separated from and mounted on the external equipment in accordance with an embodiment of the present disclosure.
Figure 2C:
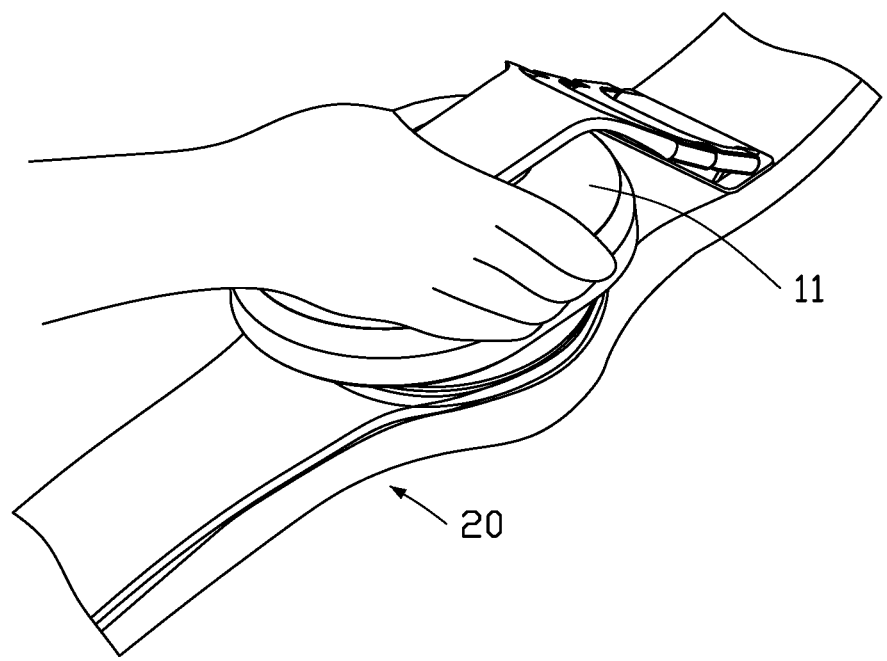

FIGS. 2B-2C respectively illustrate perspective views showing the device body 11 being separated from and mounted on the external equipment 20 in accordance with an embodiment of the present disclosure. In some instances, the device body 11 is unlocked from the bottom fixture 17 for battery replacement; thereafter, the device body 11 is fastened to the external equipment 20 by pressing the device body 11 against the bottom fixture 17. In some embodiments, the external equipment 20 is an orthosis equipment, a rehabilitation equipment, or an orthopaedic equipment. For example, the external equipment 20 is a knee brace or a splint.

Figure 3A:
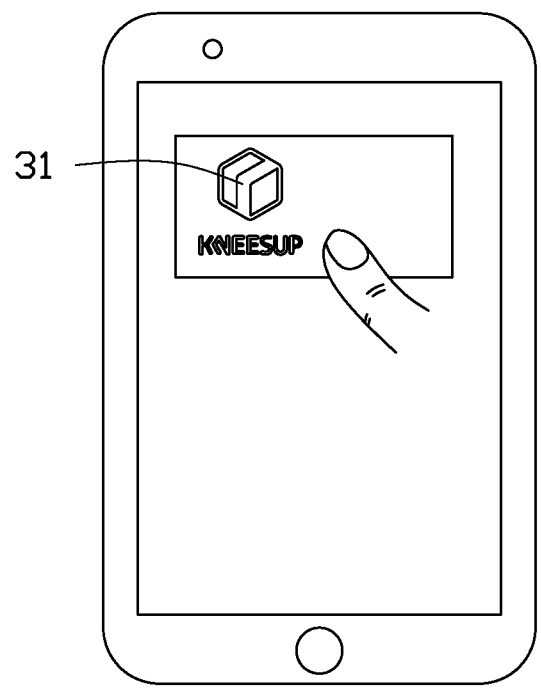
FIGS. 3A-3C are exemplary user interfaces that may be used to initiate a connection between the monitoring device assembly and an application in accordance with an embodiment of the present disclosure.
Figure 3B:
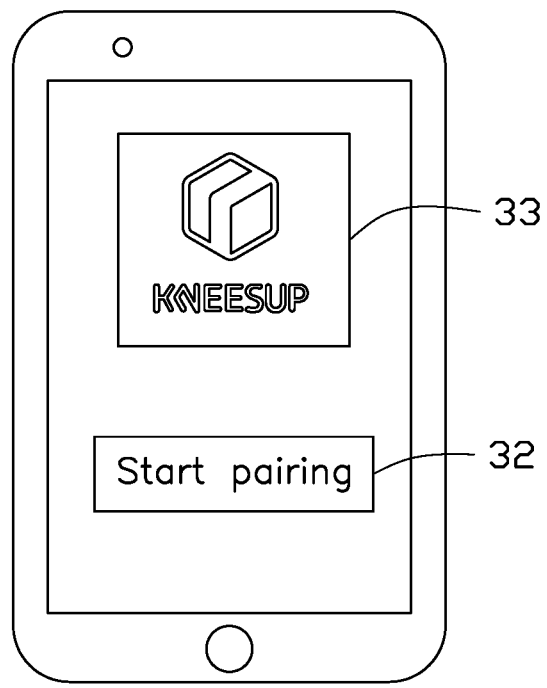
Figure 3C:
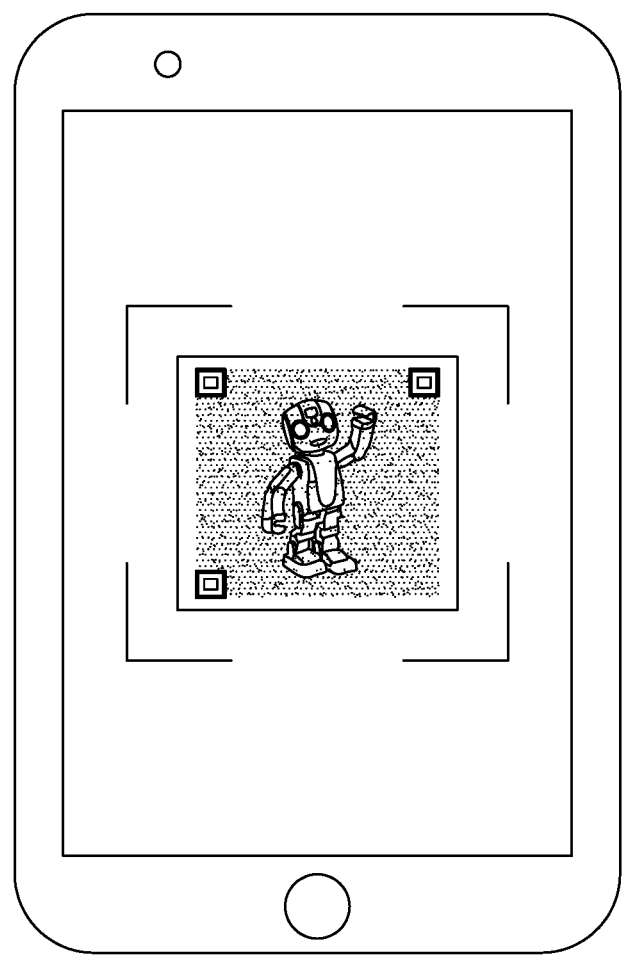

FIGS. 3A-3C illustrate exemplary user interfaces that may be used to initiate a connection between the monitoring device assembly and an application in accordance with an embodiment of the present disclosure. Once the application is downloaded to a computing device, for example, a mobile phone, a user may select an application icon 31 to initiate the application. The device registration user interface 33 may include a pairing button 32. By clicking the pairing button 32, a quick response (QR) code as shown in FIG. 3C associated with the monitoring device assembly may be provided to the user for scanning for device pairing.

FIGS. 4A-4F illustrate exemplary user interfaces that may be used to indicate the status of the monitoring device assembly and facilitate an angle calibration of the monitoring device assembly in accordance with an embodiment of the present disclosure. A user interface 400 may include a connection icon 41 for initiating the connection and calibration of the monitoring device assembly. After the connection icon 41 is clicked, the user interface 400 may display a first section 401 and a second section 402. In the first section 401, a connection status 42 may be shown to indicate whether the monitoring device assembly is connected to the computing device. A battery status 43 may further be included to indicate the remaining battery capacity of the monitoring device assembly. In the second section 402, an angle indicator 45 may be shown to indicate a current angle measured by the monitoring device assembly. The second section 402 may further include an angle calibration button 44 configured to initiate an angle calibration process.

Figure 2D:
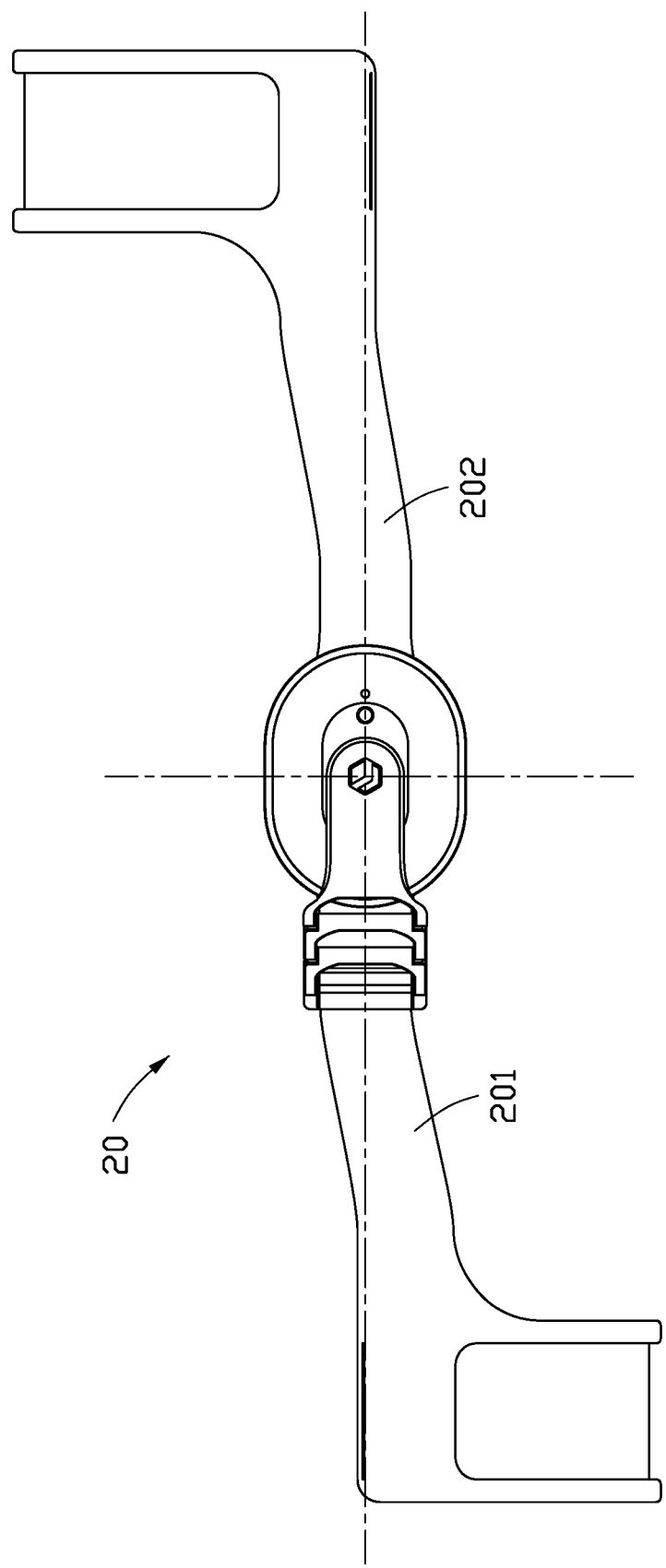
FIGS. 2D-2E are side views respectively showing the external equipment being adjusted to a particular degree in accordance with an embodiment of the present disclosure.
Figure 2E:
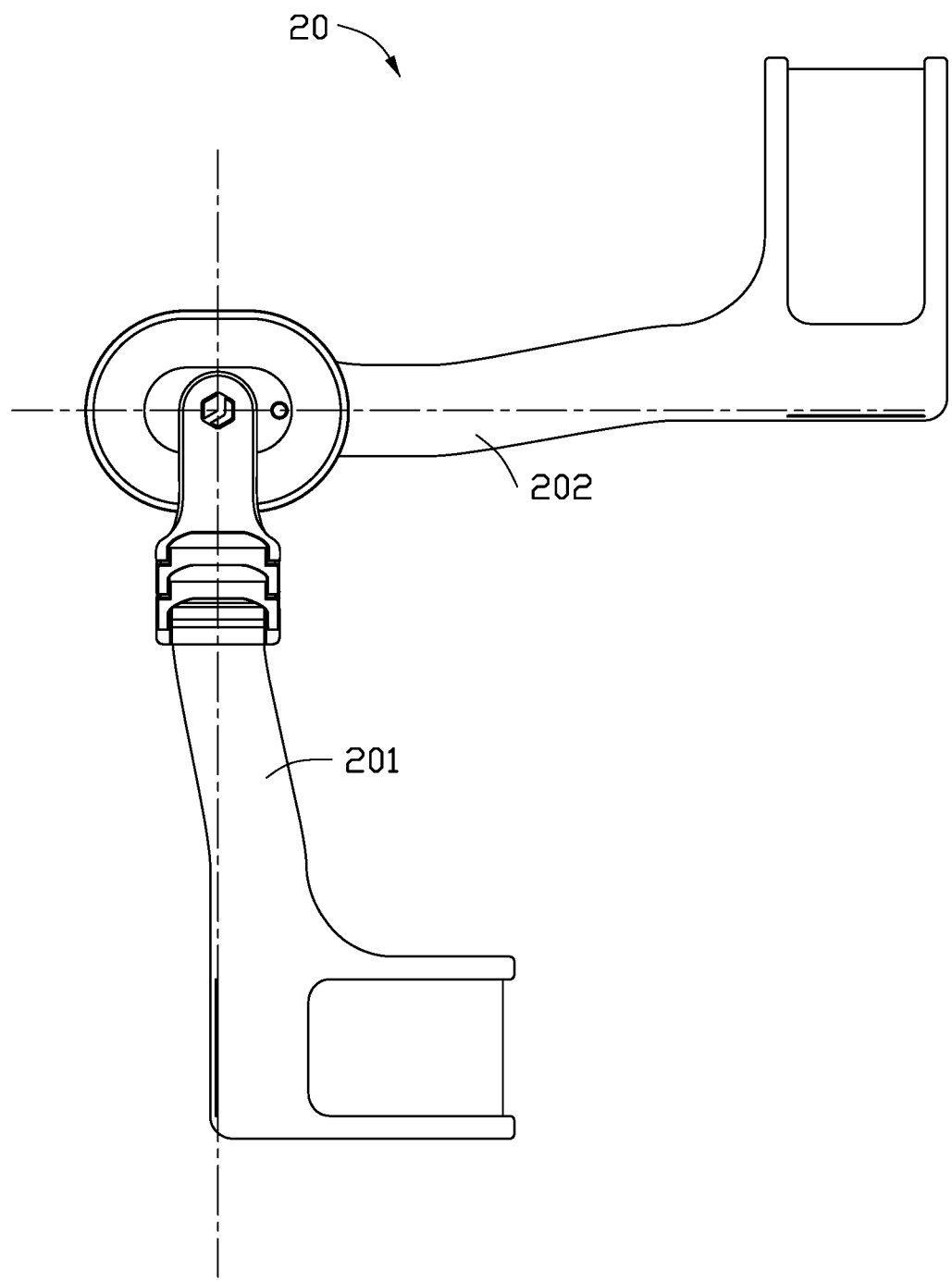
Figure 4A:
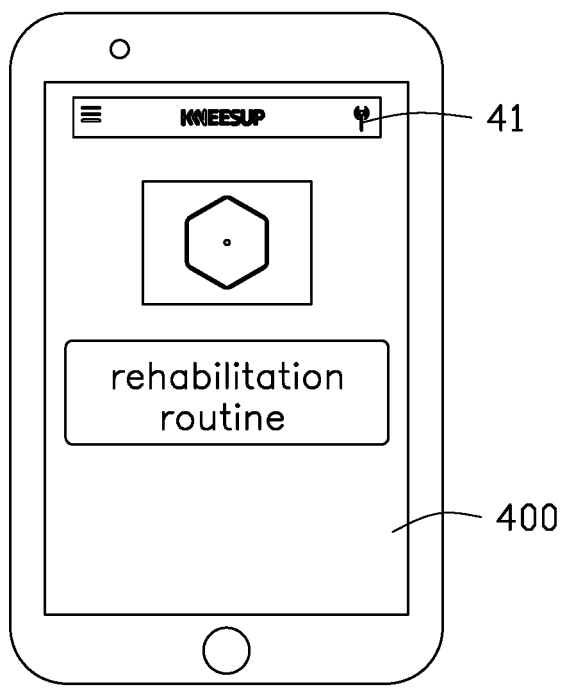
FIGS. 4A-4F are exemplary user interfaces that may be used to indicate the status of the monitoring device assembly and facilitate an angle calibration of the monitoring device assembly in accordance with an embodiment of the present disclosure.
Figure 4B:
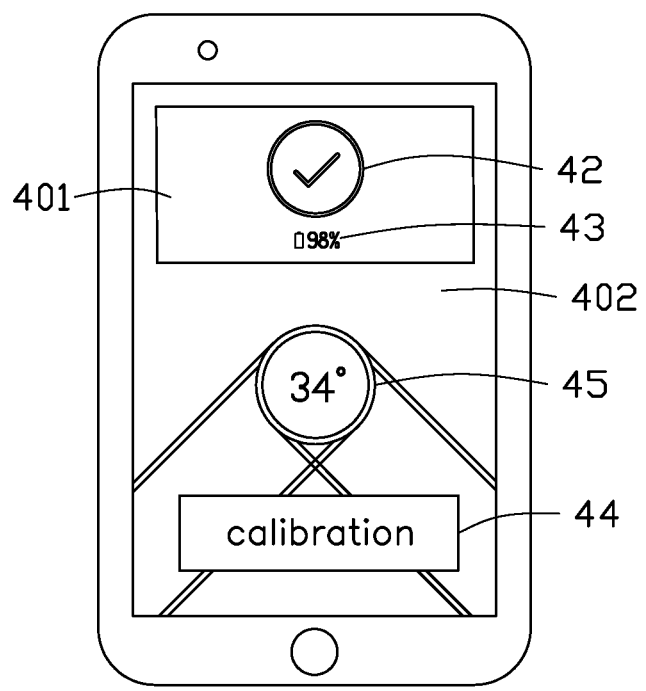
Figure 4C:
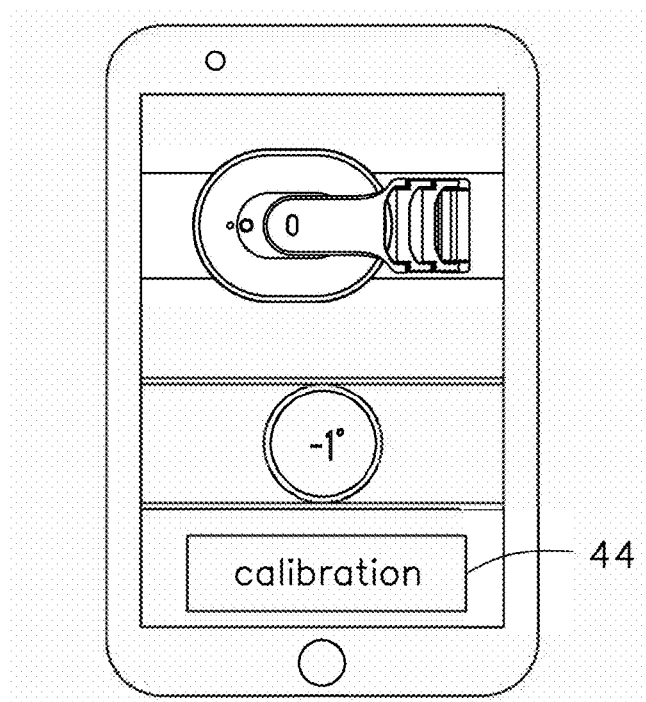
Figure 4D:
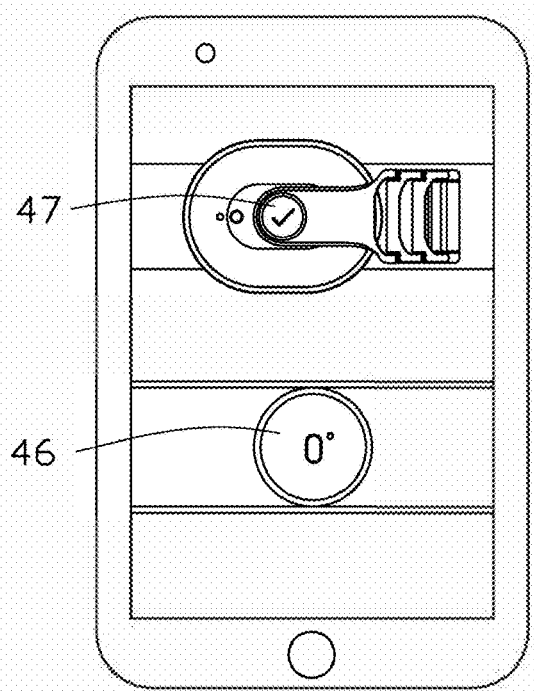
Figure 4E:
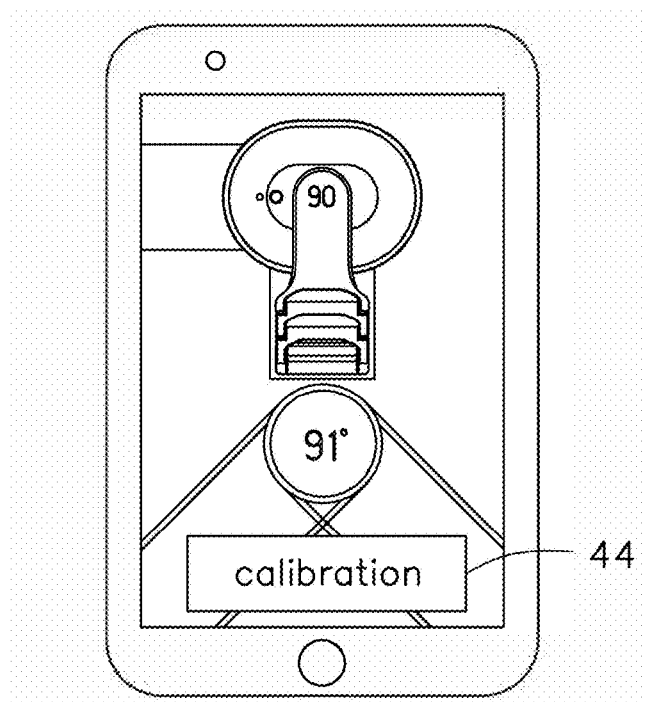
Figure 4F:
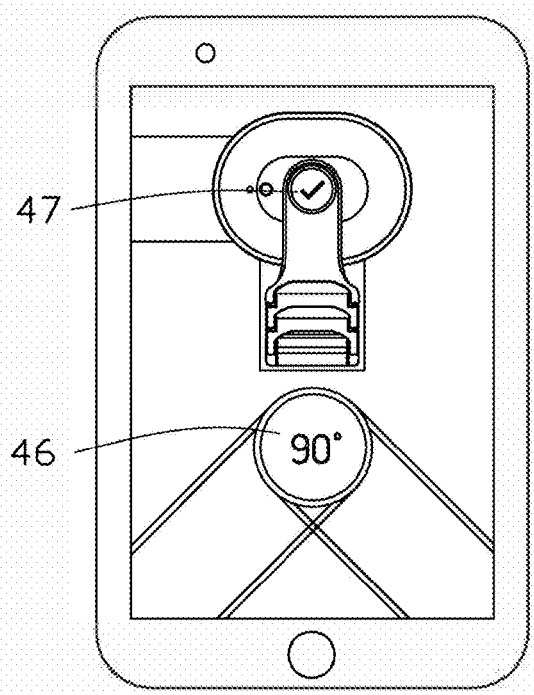

In some embodiments, prior to initiating the angle calibration, the user may be advised to setup the limit of rotation of an external equipment 20 connected to the monitoring device assembly 10 (for example, a knee brace) to fall within a range between 0 degree to 90 degrees. As illustrated in FIG. 2D, the angle formed between the first member 201 and the second member 202 of the knee brace is adjusted to 0 degree. Subsequently, the user may click the calibration button 44 for setting the angle of the monitoring device assembly to 0 degree. As illustrated in FIG. 4D, a section 46 may show a reading of 0 degree after the angle calibration. Similarly, as illustrated in FIG. 2E, when the angle of the knee brace is adjusted to 90 degrees, the user may click the calibration button 44 for calibrating the angle of the monitoring device assembly to 90 degrees. As illustrated in FIG. 4F, the section 46 may show 90 degrees after the angle calibration. Furthermore, as exemplified in FIGS. 4C-4F, the monitoring device assembly may be partially illustrated on the user interface to facilitate the calibration process; a status indicator 47 may further be displayed to indicate whether the calibration is successful.

Figure 5A:
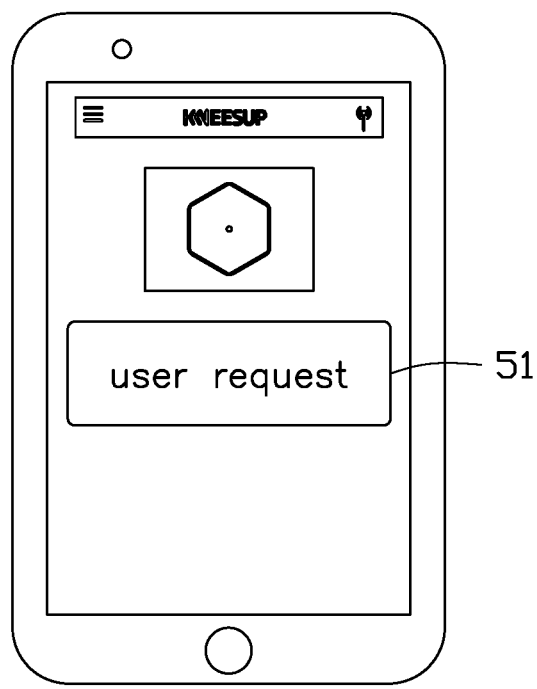
FIGS. 5A-5B are exemplary user interfaces that may be used to indicate linking between the user and an authorized personnel in accordance with an embodiment of the present disclosure.
Figure 5B:
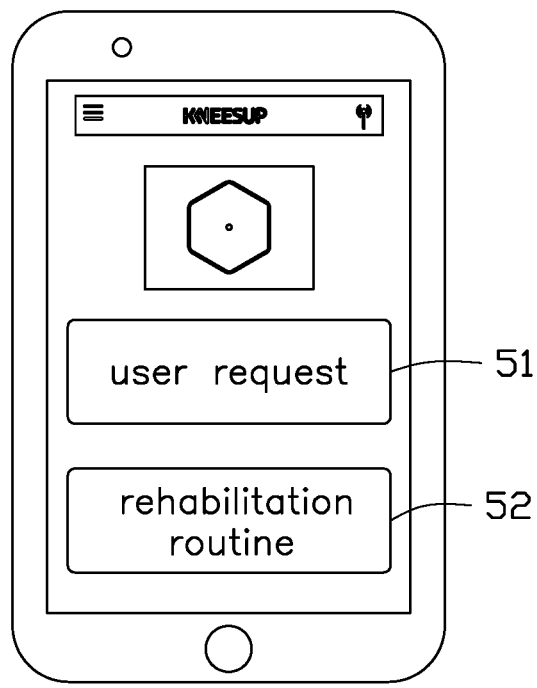

FIGS. 5A-5B illustrate exemplary user interfaces that may be used to indicate linking between the user and an authorized personnel (e.g., a doctor) in accordance with an embodiment of the present disclosure. In FIG. 5A, a section 51 may be shown to indicate that a request for linking the authorized personnel has been sent and the request is pending. In FIG. 5B, the section 51 indicates the request is approved and a section 52 may display a rehabilitation routine.

Figure 6A:
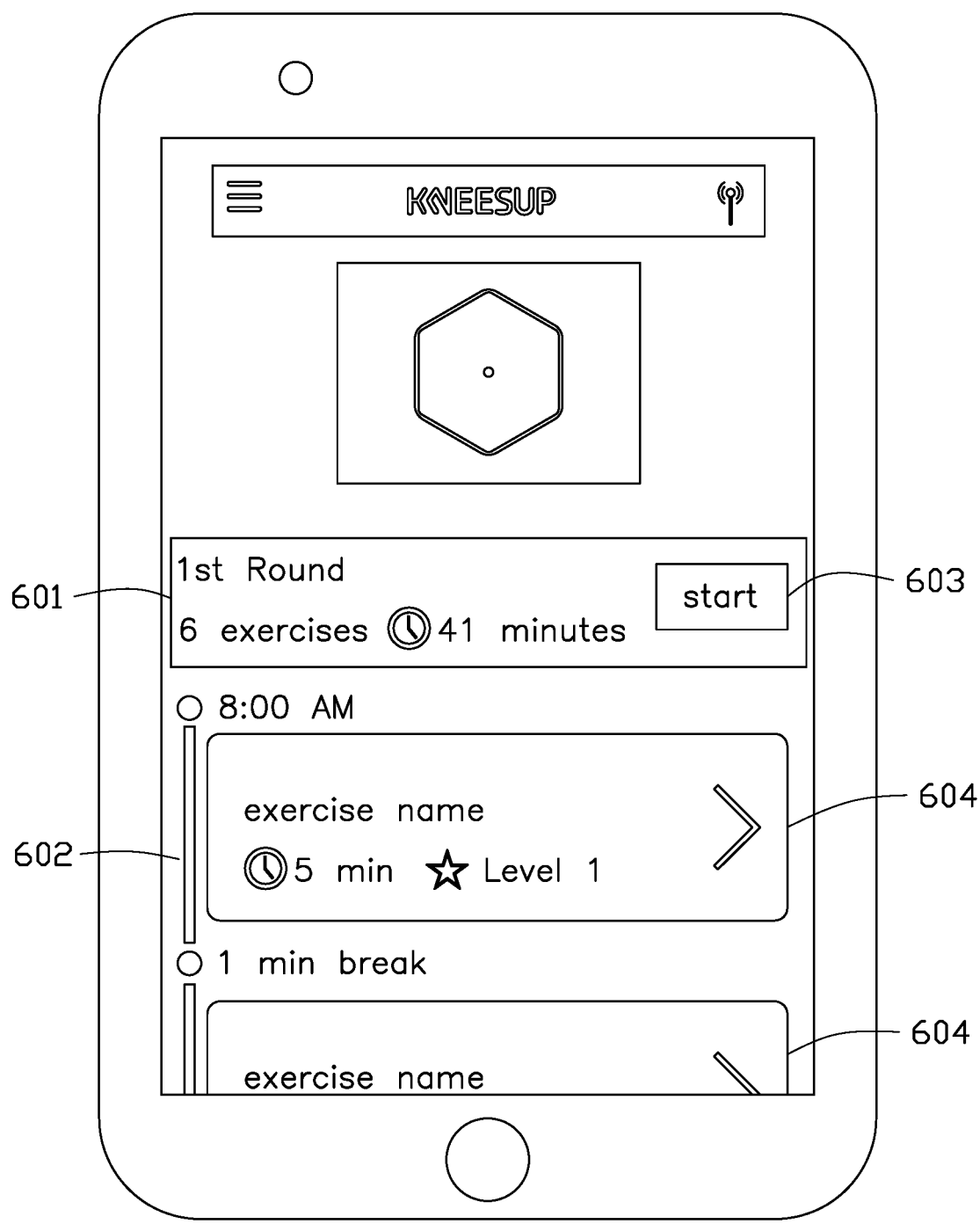
FIGS. 6A-6H are exemplary user interfaces that may be used to display contents associated with the rehabilitation routine in accordance with an embodiment of the present disclosure.

FIGS. 6A-6H illustrate exemplary user interfaces that may be used to display contents associated with the rehabilitation routine in accordance with an embodiment of the present disclosure. In FIG. 6A, a section 601 may be displayed to provide preliminary information associated with the rehabilitation routine, including round number (e.g., first round), a count of exercises of the rehabilitation routine (e.g., 6 exercises), and a predetermined duration for completing the rehabilitation routine (e.g., 41 minutes). An indicator 602 may further be displayed to provide detailed information associated with each of the exercises; for example, the indicator 602 may include a side bar, a suggested time for starting the first exercise (e.g., 8:00 AM), a list of each of the exercises, a predetermined duration for break between the exercises (e.g., 1 minute).

In some embodiments, the list may be shown by one or more exercise cards 604, each of which indicates the name of the exercise, a predetermined duration for completing the exercise (e.g., 5 minutes), and a competence level of the exercise (e.g., level 1). As illustrated in FIG. 6A, the user may initiate the rehabilitation routine by clicking a start button 603 or any exercise card 604.

Figure 6B:
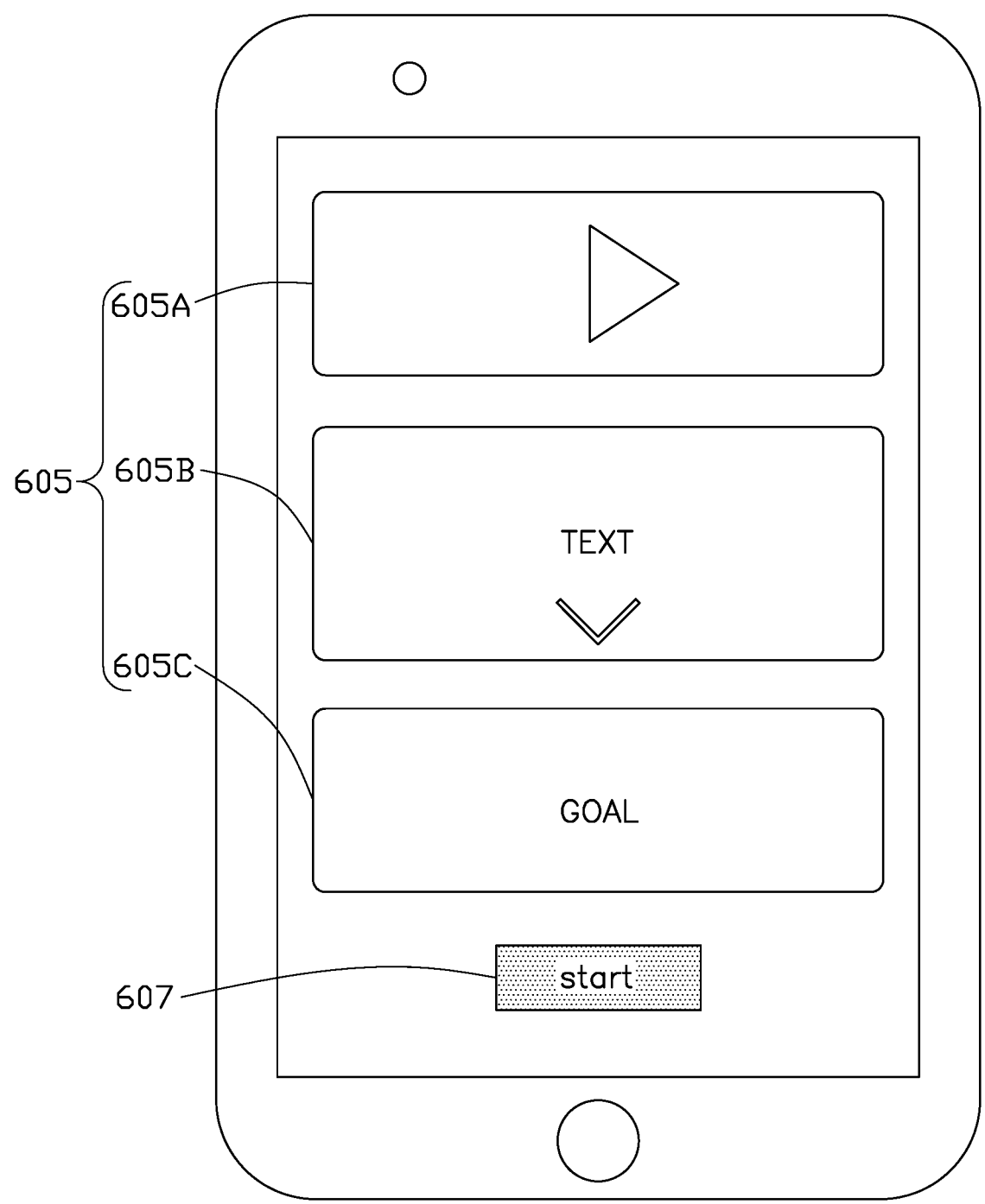

As shown in FIG. 6B, after the rehabilitation routine is initiated, a section 605 may be displayed to provide an instruction associated with the exercise. The section 605 may include, for example, a video 605A, a text 605B, and a goal 605C. The video 605A may demonstrate postures for performing the exercise. The text 605B may elaborates the postures for performing the exercise. The goal 605C may include a minimum goal and a target goal. In some examples, the minimum goal is 80 degrees and the target goal is 90 degrees. In other examples, minimum goal and the target goal may be metrics such as time, calories, steps, rate, length, or percentage.

Figure 6C:
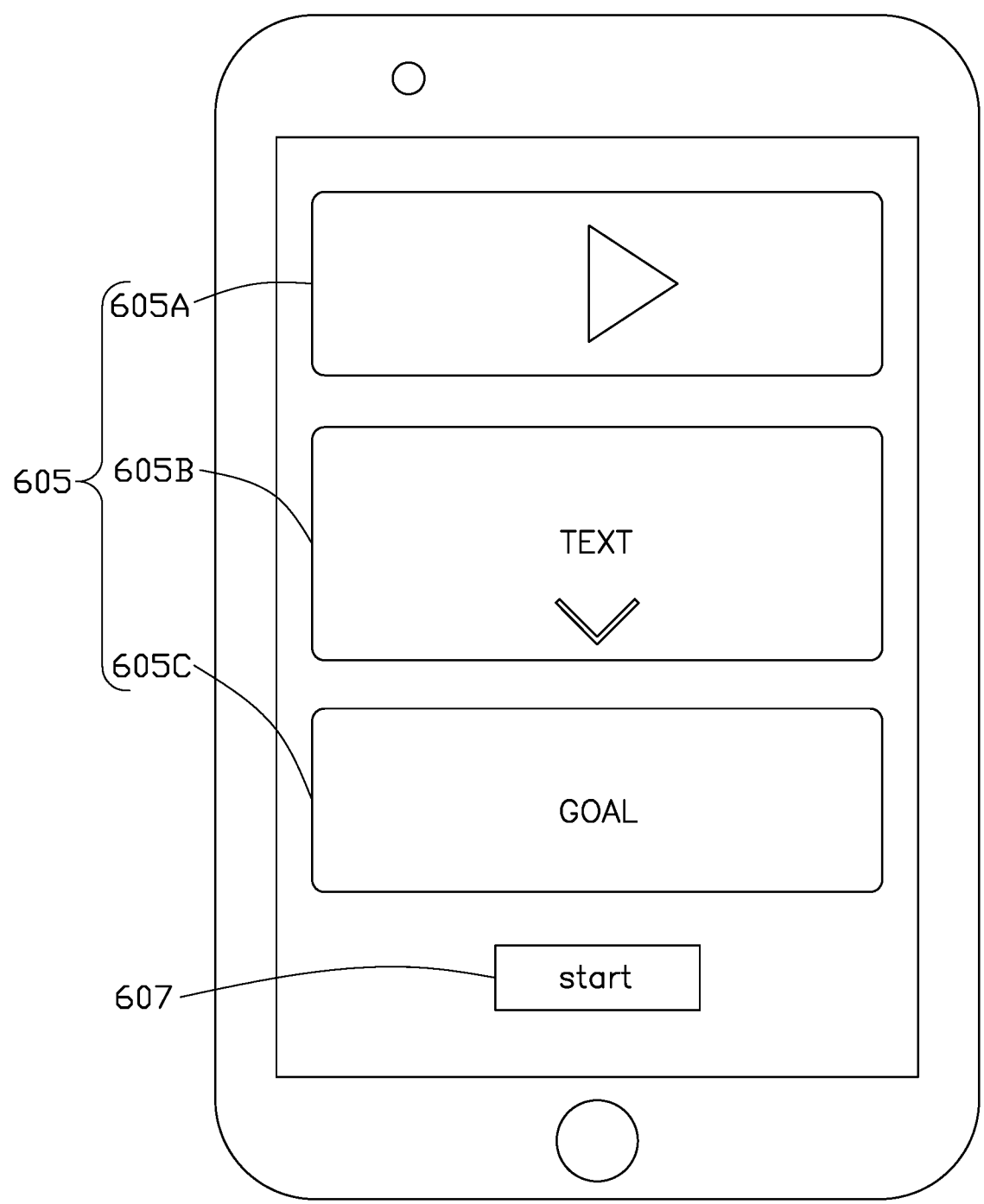

For the purpose of preventing the user from harm caused by performing the exercise, a start button 607 on the user interface may be disabled if a play record of the video 605A is null (i.e., an execution history of the video is empty). For example, as shown in FIG. 6B, if it is the first time for the user to perform the exercise, the user would be required to watch the video 605A before starting the exercise. Once the execution of the video 605A is completed, the start button 607 is enabled for the user to proceed to a subsequent user interface, as shown in FIG. 6C. In some embodiments, the start button 607 is disenabled if a predefined area of the text 605B is hidden. For example, the text 605B in FIG. 6B is partially displayed. The user would be required to scroll down to the end of the text 605B before starting the exercise.

Figure 6D:
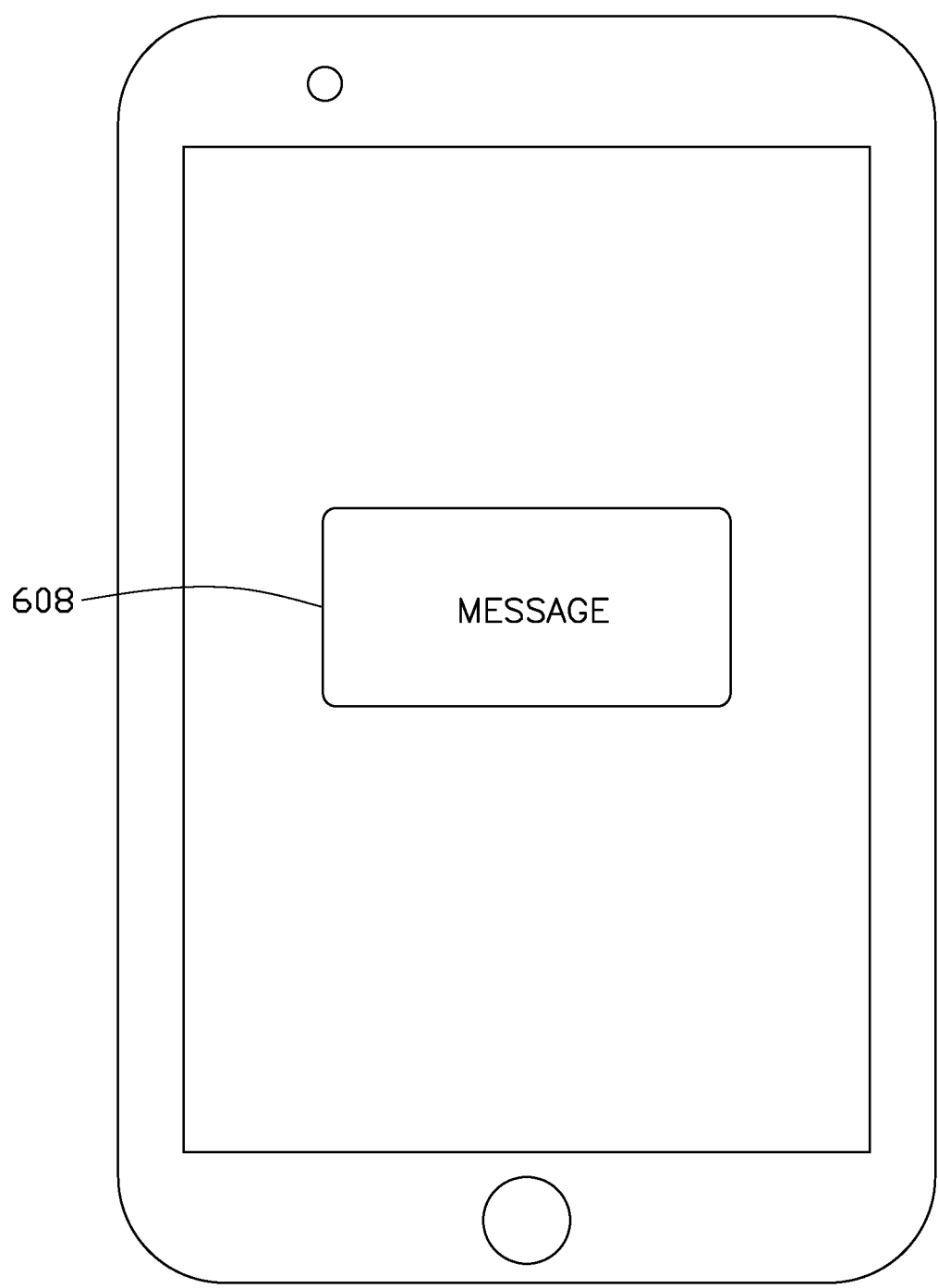
Figure 6E:
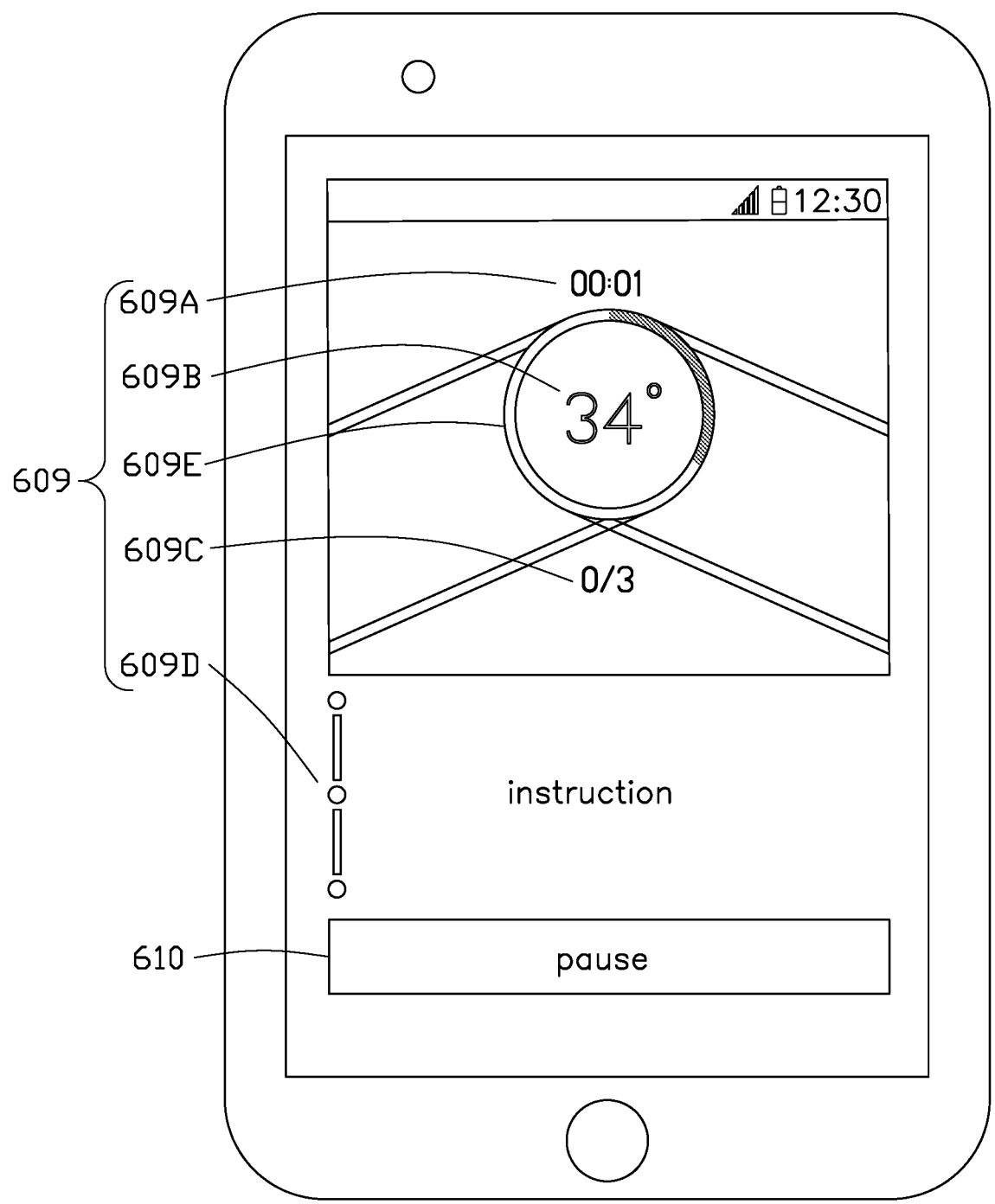
Figure 6F:
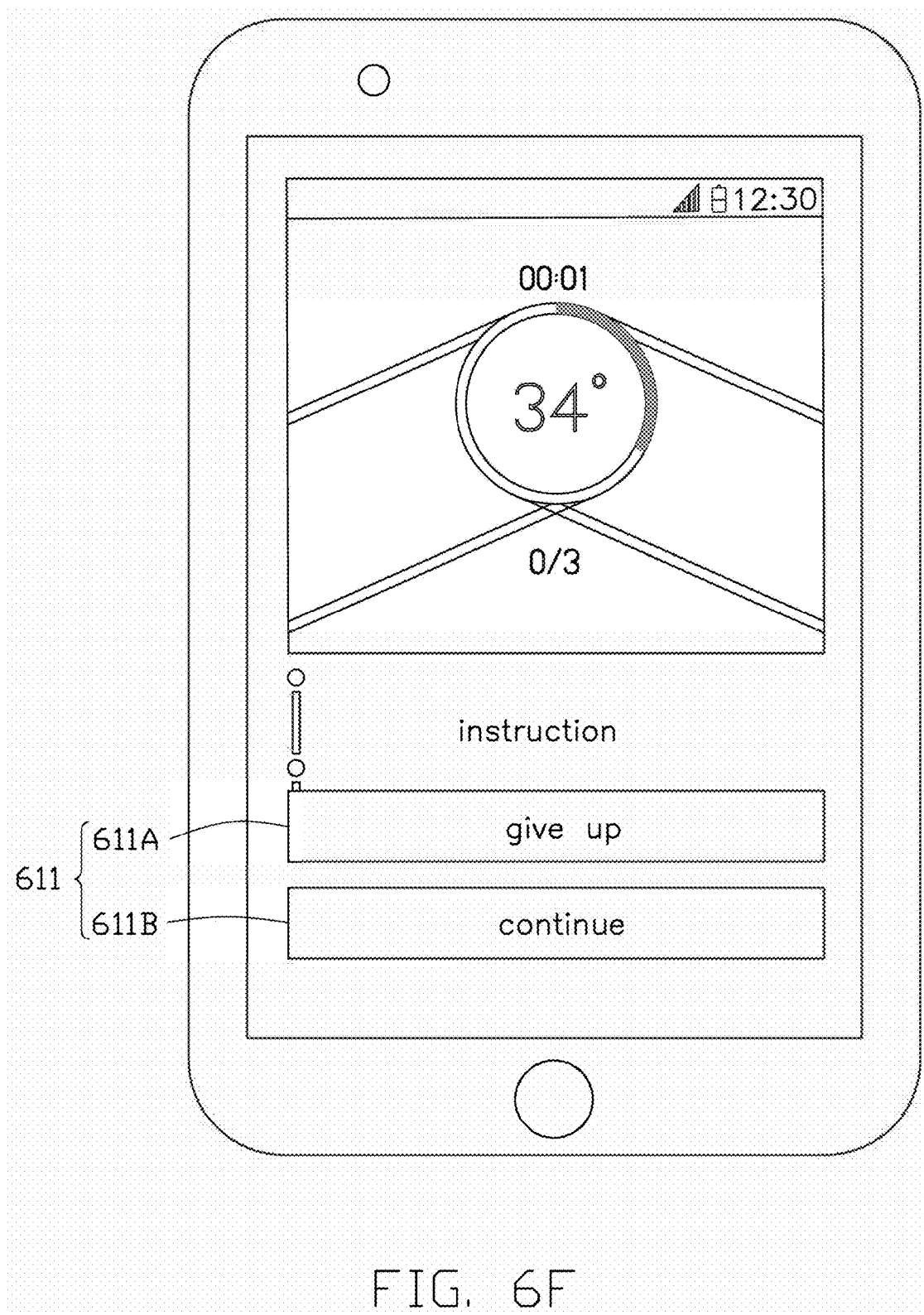

In FIG. 6D, a section 608 may be displayed to provide a message indicating that an assessment of the exercise would begin in a predetermined period of time. For example, the user may be prompted to begin the exercise after a count down. In FIG. 6E, a section 609 may be displayed to indicate various statuses of the exercise; the section 609 may include an exercise time 609A, an exercise metrics 609B, an exercise count 609C, an exercise instruction 609D, and a goal indicator 609E.

In one arrangement as shown in FIG. 6E, the exercise time 609A may indicate an elapsed time of the assessment. The exercise metrics 609B may be an indication of movement associated with the exercise. The exercise count 609C may include a dynamic digit and a fixed digit. The dynamic digit represents a number of counted exercise. The fixed digit is a predetermined count of the exercise. The goal indicator 609E may show a progress made toward the goal 605C.

In some embodiments, the progress made toward the goal 605C may be visualized as an object, for example, a ring-shaped object as exemplified in FIG. 6E. As the exercise metrics 609B exceeds the minimum goal, the ring may begin to change the appearance (e.g. color or shape). In an embodiment, a calculation of a percentage of an elapsed time over a predefined value may start once the minimum goal is reached and held. A portion of the ring may be modified (e.g. displaying a different color) according to the calculated percentage. In one example, if the calculated percentage is 50% (e.g., the elapsed time is 5 seconds and the predefined value is 10 seconds), half of the ring may be colored and the remaining half thereof may be transparent, semi-transparent, or remain unchanged. The calculation may reset if the exercise metrics 609B fall below the minimum goal during the calculation. Other visual effects may be utilized to emphasize the difference between a percentage of the goal 605C remained to be achieved and a percentage of the goal 605C already completed.

In one example, the exercise instruction 609D provides step-wise descriptions of the exercise for the user wearing the external equipment 20 and the monitoring device assembly 10 to follow. As exemplified in FIG. 6E, the steps may include: (1) increase pressure to bend the knee to an angle of 90 degrees; (2) stay at the angle for 90 seconds; and (3) release pressure and straighten the knee. The exercise metrics 609B shows a degree indicating an angle between the first member 201 and the second member 202 of the external equipment 20. The exercise metrics 609B may change dynamically during the exercise. The exercise instruction 609D may further include one or more requirements for achieving the goal 605C. For example, a first requirement may be to stay at the angle for 90 seconds, and a second requirement may be to meet the first requirement for three times. In some instances, the exercise count 609C may be configured to indicate the second requirement and the progress made toward the second requirement.

The user interface may further include a pause button 610 for pausing the assessment of the exercise. As exemplified in FIG. 6F, when the pause button 610 is clicked, a section 611 may be displayed to provide a button 611A for terminating the assessment, and a button 611B for continuing the assessment. In order to prevent unintentional termination, the user may be required to press the button 611A for a predefined period of time to complete termination.

Figure 6G:
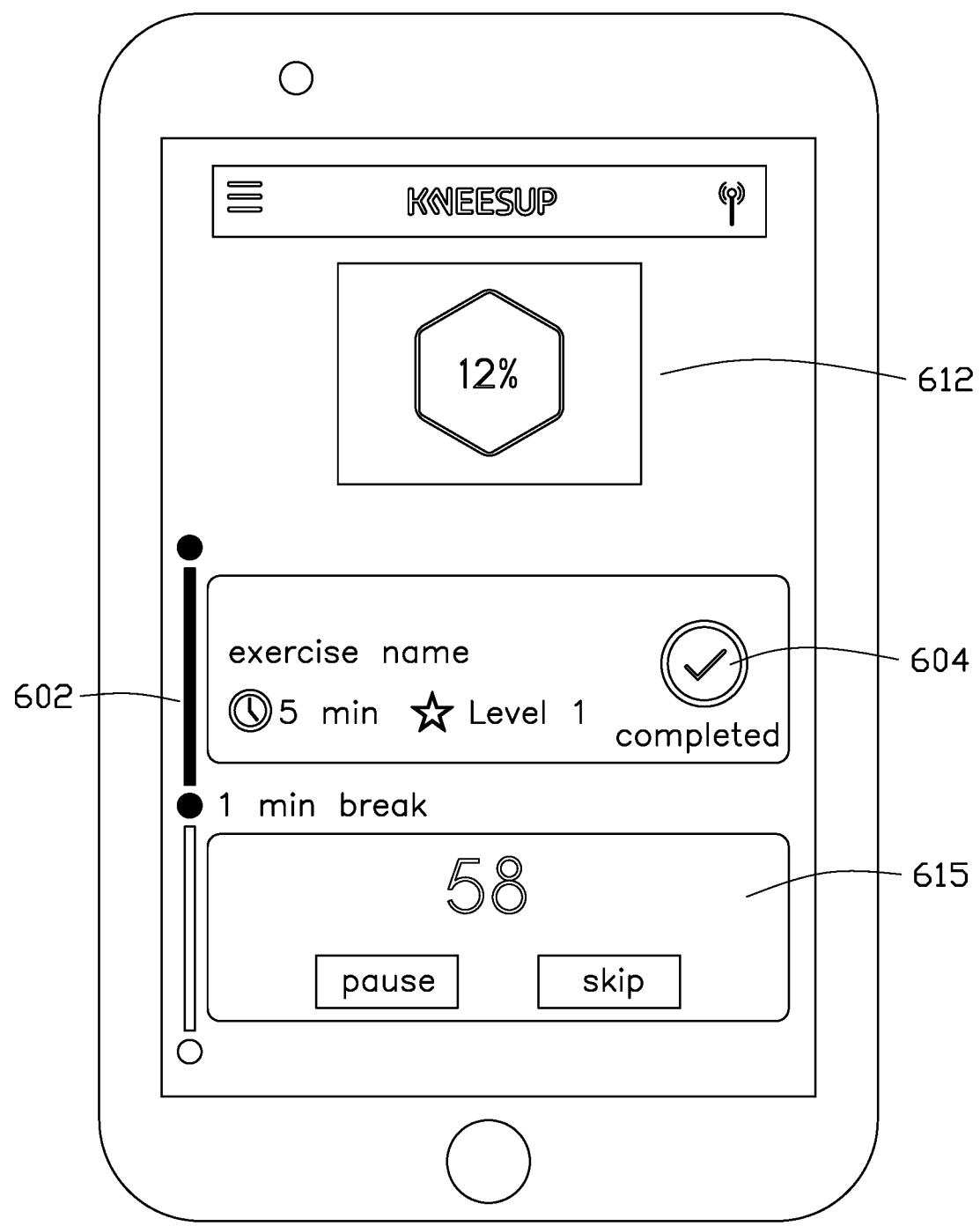

As shown in FIG. 6G, after the assessment of the exercise is completed, a section 612 may be displayed to indicate a progress made toward the rehabilitation routine, and the corresponding exercise card 604 and the indicator 602 may be updated in accordance with the assessment of the exercise.

In some embodiments where the goal 605C is achieved, the section 612 or a dashboard may show a percentage of completion of the rehabilitation routine, and a count of exercise left to be performed. The exercise card 604 may display a mark for indicating that the exercise is completed. A portion of the side bar corresponding to the completed exercise may also be modified (e.g., displaying in a different color). A section 615 may further be displayed and overlays a subsequent exercise card. The section 615 may include a countdown timer, a button for pausing the countdown timer, and a button for skipping the countdown timer. As the countdown time is up or skipped, an assessment of a subsequent exercise may begin.

Figure 6H:
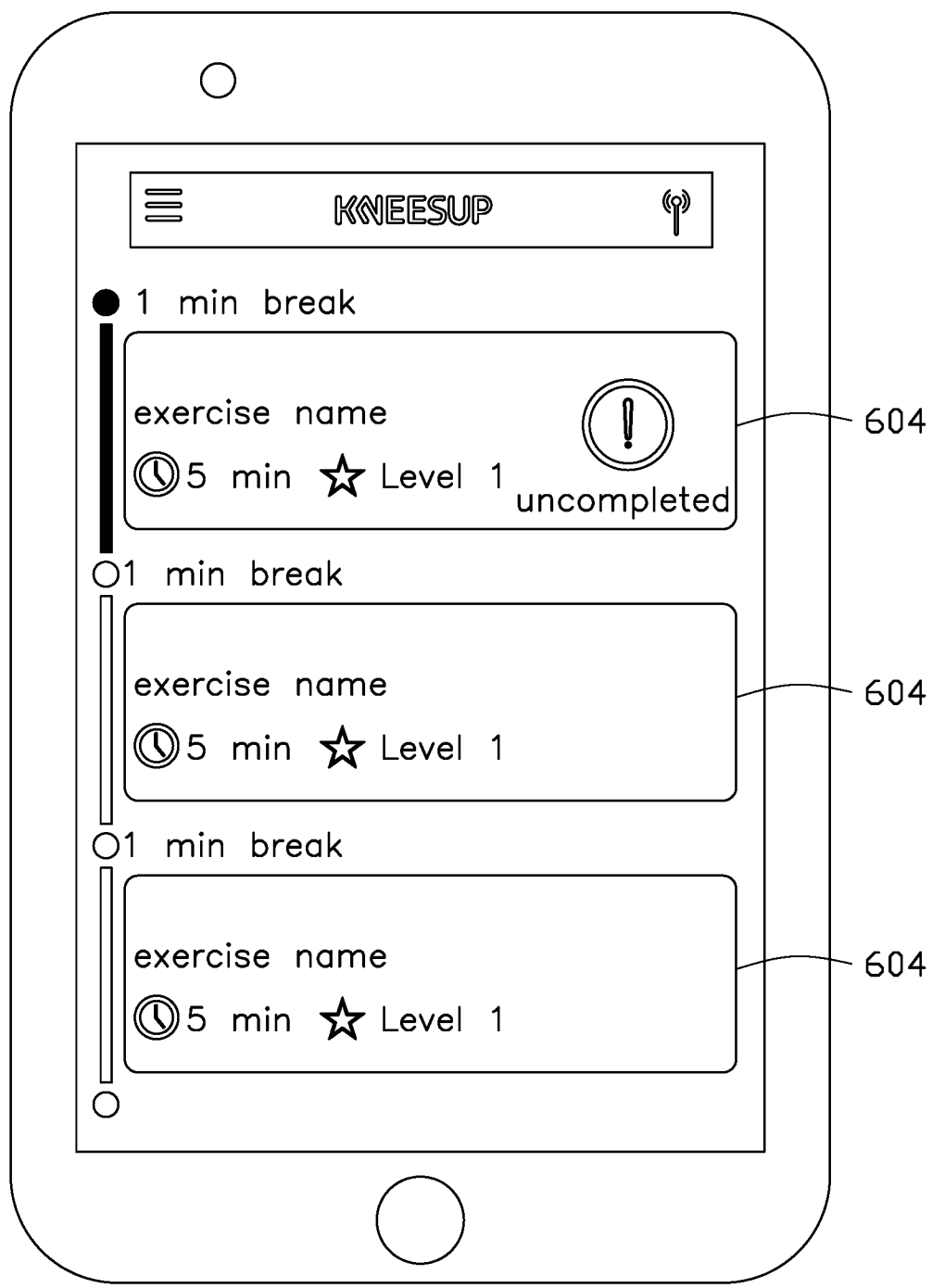

In other embodiments where the rehabilitation routine is discontinued by, for example, user termination of the assessment of the exercise or an exercise time 609A that exceeds a predetermined value, the exercise card 604 may be configured to show a mark for indicating that the exercise is uncompleted, as shown in FIG. 6H. A portion of the side bar 602 corresponding to the uncompleted exercise may also be modified (e.g., displaying a different color). In the embodiments, access to the exercise card 604 may be disabled; for example, the exercise card 604 may become unclickable. In some embodiments, an access to the exercise card 604 may be disabled for a predetermined period of time for the purpose of preventing the user from the harm caused by performing the exercise repeatedly. The user may choose the other clickable exercise card(s) to continue the rehabilitation routine.

Figure 7:
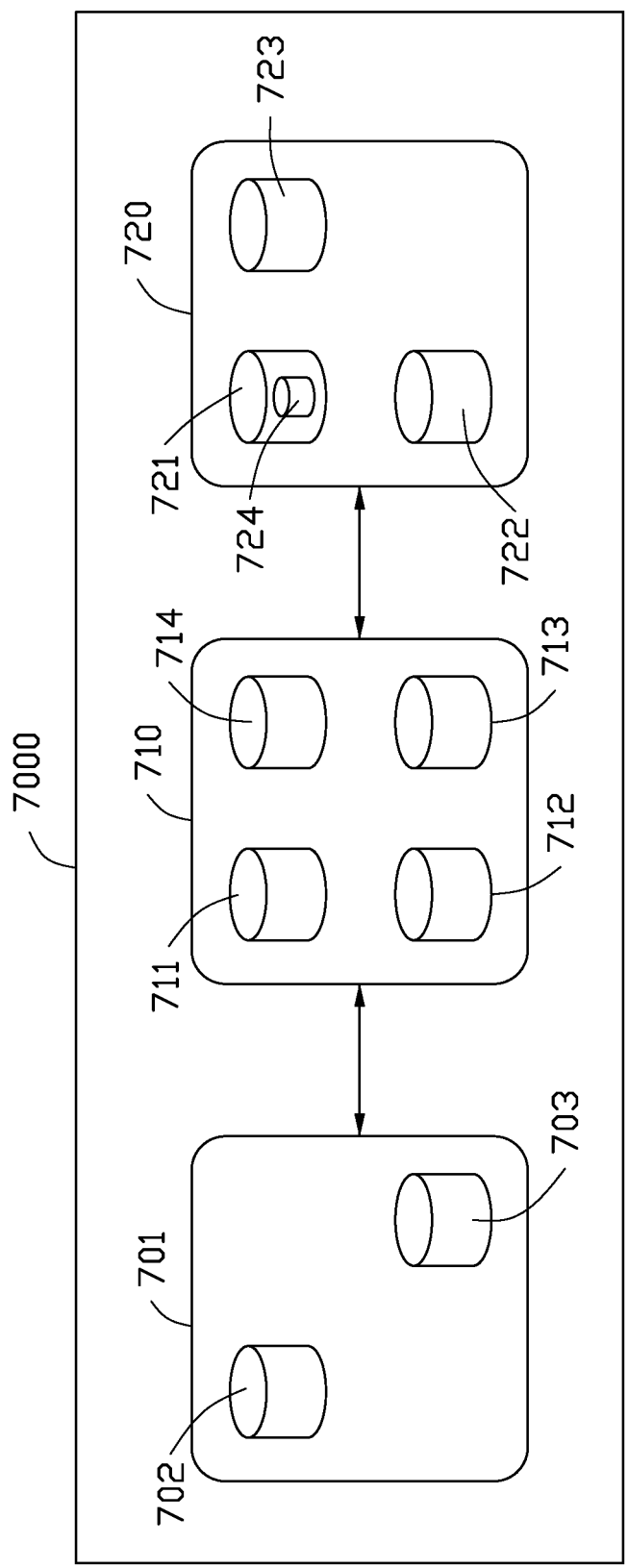
FIG. 7 is a schematic block diagram of a rehabilitation system in accordance with an embodiment of the present disclosure.

FIG. 7 illustrates a schematic block diagram of a rehabilitation system 7000 in accordance with an embodiment of the present disclosure. The rehabilitation system 7000 may include an input device 701, a computing device 710, and a server 720.

The input device 701 may be the monitoring device assembly 10. The input device 701 may include one or more inertial measurement units (IMU) or sensors 702. The sensors may include a g-sensor (or accelerometer), a gyro-sensor (or gyroscope), an m-sensor (or electrical compass), an o-sensor (or orientation sensor), a position sensor, a proximity sensor, an ambient sensor, a thermometer, a pressure sensor, and a pedometer. The input device 701 may further include a camera or a video recorder.

The computing device 710 may include one or more processors 711 configured to execute program instructions, and a memory 713 including volatile and non-volatile memory such as random access memory (RAM) and readonly memory (ROM). The memory 713 may be configured to store the program instructions, the indication of movement associated with the exercise, the assessment of the exercise, and a user profile. Specifically, the user profile may include personal information, electronic medical record (EMR), rehabilitation routines and/or other data associated with the user. The computing device 710 may further include a display area 714.

In some embodiments, the input device 701 may include a transmitter 703, and the computing device 710 may include a receiver 712. The receiver 712 is configured to receive data from the transmitter 703. For example, after a connection between the input device 701 and the computing device 710 is established, the transmitter 703 may transmit measurement data to the receiver 712.

In some embodiments, the input device 701 provides sensed or detected data to the computing device 710 for calculating the indication of movement associated with the exercise. An algorithm may be used during such calculation. The indication of movement may be a range of motion, a posture, stability, balance, a pattern of movement, a repetition, vibration, velocity, a time period of movement, or a length of time for holding a particular posture. In one example, a single input device attached to a predefined portion of the body may be used to provide monitored data to the computing device 710 for calculating the indication of movement associated with the exercise of the body portion.

In some examples where the user wearing the monitoring device assembly performs a forward straight leg raise exercise, the sensor chip including a g-sensor and a vibration g-sensor may be used to provide measurement data to the input device 701. Such measurement data is transmitted to the computing device for deriving the indication of movement. Based on the measurement data, the derived indication of movement may include an angle of knee flexion, a height from knee to ground, and a trace of a joint movement. The computing device uses the indication of movement for assessing the exercise being performed by the user. The assessment may further include a diagnosis of the exercise. For example, based on the angle of knee flexion and the trace of the joint movement, external rotation, internal rotation, and/or abduction of a lower extremity may be diagnosed. Furthermore, the assessment of a particular posture or movement may include a comparison of the indication of movement with one or more predefined values. For example, once the angle of knee flexion and the height from knee to ground satisfy a predefined requirement, the computing device may begin to count the time period for which the user holds the posture. The computing device may further compare the time period with a predefined threshold for evaluating a progress of the user on performing the exercise.

In some embodiments, the diagnosis or an evaluation of the exercise may be strength, power, endurance, agility, stability, balance, proprioception, mobility, performance symmetry, or movement quality. The diagnosis or the evaluation may be based on data monitored by the monitoring device assembly 10.

In some embodiments, program instructions associated with the indication of movement and/or the assessment of the exercise may be executed on the input device or the server. The rehabilitation system 7000 may further include a gateway (not shown) for executing the program instructions. Edge or fog computing technology may be used in the computing device and the gateway.

Still referring to FIG. 7, the server 720 may include a storage device 721, a management agent 722, and an intelligence engine 723. The storage device 721 may be configured to store program instructions to be executed by the server, and one or more instruction data such as video, image, text, and parameter associated with the exercise. A data synchronization may be performed between the computing device and the server. Therefore, the storage device 721 may further store the indication of movement associated with the exercise, the assessment of the exercise, and the user profile. Optionally, the storage device 721 may further include a database 724.

The management agent 722 may be configured to allow an authorized personnel to at least access, retrieve, manage, and/or modify stored data. The authorized personnel may be an administrator, a doctor, a therapist, or a healthcare practitioner. The authorized personnel may login on the platform to review a request submitted from the user (e.g., a patient). Based on an evaluation of the user profile, the authorized personnel may select a rehabilitation routine from a preset routine or generate a customized routine. The selected rehabilitation routine including the one or more instruction data may be assigned to the user profile by the authorized personnel. Subsequent to an approval of the request, the user profile in the computing device may be updated. In some instances, the management agent 722 is a platform, a host, or a website.

The intelligence engine 723 may be configured to generate a smart rehabilitation routine based on stored data. For example, the intelligence engine 723 may analyze the user profile in accordance with the data in the database 724. In some examples, the user may be required to perform one or more movements with the monitoring device assembly worn on them for providing additional inputs for analyzing a condition of the user. Based on the analysis, the intelligence engine 723 may generate the smart rehabilitation routine or an arrangement of the one or more instruction data. The intelligence engine 723 may further assign the smart rehabilitation routine to the user profile or add the smart rehabilitation routine to the preset routine (i.e., output a preset rehabilitation routine). In some instances, the intelligence engine may be placed elsewhere in the system and independently from the server 720. In some aspects, the rehabilitation system 7000 is artificial intelligence (AI) powered.

Figure 8:
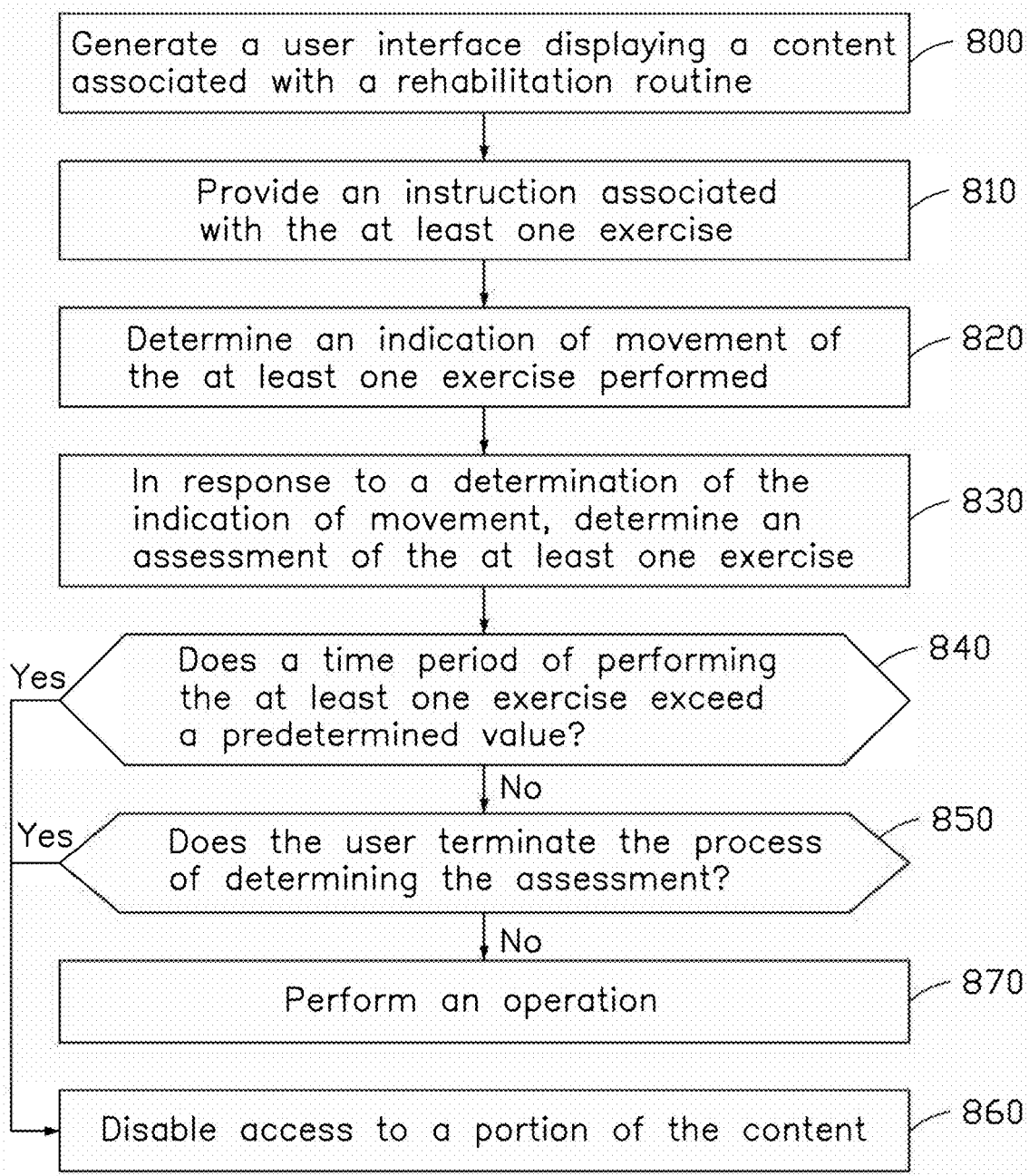
FIG. 8 is a flowchart illustrating exemplary operations of an exemplary rehabilitation system configured to assess one or more movements of one or more exercises performed by a person wearing the monitoring device assembly in accordance with an embodiment of the present disclosure.

FIG. 8 is a flowchart illustrating exemplary operations of an exemplary rehabilitation system configured to assess one or more movements of one or more exercises performed by a person wearing the monitor device assembly in accordance with an embodiment of the present disclosure. The process shown in FIG. 8 may be performed by one or more processors of a computing device. For purposes of illustration, FIG. 8 is described below within the context of FIGS. 6A-6H and 7.

As shown in step 800, the computing device 721 may generate a user interface displaying a content associated with a rehabilitation routine. For example, when the application is executed, the display area 714 may display the section 601, the indicator 602, the start button 603, and the exercise card 604.

As shown in step 810, the computing device 721 may provide an instruction associated with at least one exercise in the rehabilitation routine. For example, the display area 714 may display the video 605A demonstrating a posture of the at least one exercise.

As shown in step 820, the computing device 721 may determine an indication of movement of the at least one exercise. For example, the one or more processors 711 may derive indication of movement by calculating data provided from the one or more sensors 702 in the input device.

As shown in step 830, the computing device 721 may determine an assessment of the at least one exercise in response to a determination of the indication of movement. For example, the assessment may include comparing, contrasting, or otherwise analyzing the indication of movement with relevant data.

As shown in steps 840 and 860, whether a time period of performing the at least one exercise exceeds a predetermined value is determined. The computing device 721 may disable access to a portion of the content if the time period of performing the at least one exercise exceeds a predetermined value. Alternatively, the computing device 721 may proceed to step 850.

As shown in steps 850 and 860, whether the user terminates the process of determining the assessment is determined. The computing device 721 may disable access to a portion of the content if the user terminates the assessment. Alternatively, the computing device 721 may proceed to step 870.

As shown in step 870, the computing device 721 may perform an operation based on the determinations that the time period of performing the at least one exercise does not exceed the predetermined value and that the user did not terminate the assessment. The operation to be performed by the computing device 721 may include updating the section 612, the exercise card 604, and the indicator 602.

The various embodiments of the present disclosure provide numerous benefits. In one aspect, the monitoring device assembly can be easily mounted to any wearable device, for example, a knee brace. In another aspect, the system provides a real-time evaluation of the exercise performed. It reduces the risk of harm during performing the exercise. It further informs the users the accuracy of the movements being performed. In another aspect, the system improves the efficiency of diagnosis. Healthcare providers may remotely adjust the rehabilitation routine when the monitored data indicates an improvement made by the patient or deterioration of the condition of the patient.

The terminology used herein is for the purpose of describing particular embodiments only and is not intended to be limiting of embodiments of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to embodiments of the present disclosure in the form disclosed. Many modifications and variations will be apparent to those of ordinary skill in the art without departing from the scope and spirit of embodiments of the present disclosure. The embodiment was chosen and described in order to best explain the principles of embodiments of the present disclosure and the practical application, and to enable others of ordinary skill in the art to understand embodiments of the present disclosure for various embodiments with various modifications as are suited to the particular use contemplated.

Although specific embodiments have been illustrated and described herein, those of ordinary skill in the art appreciate that any arrangement which is calculated to achieve the same purpose may be substituted for the specific embodiments shown and that embodiments of the present disclosure have other applications in other environments. This present disclosure is intended to cover any adaptations or variations of the present disclosure. The following claims are in no way intended to limit the scope of embodiments of the present disclosure to the specific embodiments described herein.

Various examples have been described. These and other examples are within the scope of the following claims.

What is claimed is:

1. A system, comprising:
an input device configured to monitor at least one exercise performed by a user; and
a computing device comprising:
one or more processors; and
at least one memory coupled to the one or more processors and storing program instructions that when executed by the one or more processors cause the one or more processors to:
generate a user interface displaying a content, the content comprising an exercise list and the exercise list comprising at least one exercise card;
access a first exercise card in the exercise list in order to provide an instruction associated with a first exercise corresponding to the first exercise card;
determine, based on data from the input device, an indication of movement associated with the first exercise;
determine, based on the indication of movement, an assessment of the first exercise;
perform, based on the assessment of the first exercise, an operation; and
in response to a discontinuation of the assessment of the first exercise, disable access to the first exercise card in the exercise list within a predetermined time.

2. The system of claim 1, wherein the operation comprises:
updating, in response to the indication of movement exceeding a predetermined threshold, the content to indicate a progress made toward an exercise goal.

3. The system of claim 1, wherein the discontinuation comprises:
a termination caused by the user; or
a determination that an exercise time of the first exercise exceeds a predetermined value.

4. The system of claim 1, wherein the content further comprises:
a progress indicator,
wherein the program instructions, when executed, further cause the one or more processors to, after accessing the first exercise card from the exercise list, provide the instruction associated with the first exercise corresponding to the first exercise card.

5. The system of claim 4, wherein the program instructions, when executed, further cause the one or more processors to:
execute executable data associated with the instruction associated with the first exercise at least once if an execution history of the executable data is empty.

6. The system of claim 1, wherein the input device is configured to mount on a wearable device, the wearable device comprising one of an orthosis equipment, a rehabilitation equipment, and an orthopaedic equipment.

7. The system of claim 1, wherein the input device comprises one of a g-sensor, a gyro-sensor, an m-sensor, an o-sensor, a position sensor, a proximity sensor, an ambient sensor, a thermometer, a pressure sensor, a pedometer, and a camera.

8. The system of claim 1, wherein the indication of movement comprises at least one of a range of motion, a posture, stability, balance, a pattern of movement, a repetition, a vibration, a velocity, a time period of movement, or a length of time for holding a particular posture.

9. The system of claim 1, further comprising:
a server for exchanging a profile of the user with the computing device, the server comprising:
a storage device configured to store at least:
second program instructions to be executed by the server;
the indication of movement;
the assessment of the first exercise;
one or more instruction data; and
a database.

10. The system of claim 9, wherein the server further comprises an intelligence engine, and the second program instructions stored in the storage device, when executed by the intelligence engine, cause the intelligence engine to:
assign at least one of the one or more instruction data to the profile by at least:
accessing the database;
generating an analysis based on the profile and the database;
selecting, based on the analysis, the at least one of the one or more instruction data; and
updating the profile.

11. The system of claim 9, wherein the server further comprises a management agent configured to allow an authorized personnel to at least:
access the management agent; and
assign at least one of the one or more instruction data to the profile.

12. The system of claim 1, wherein the program instructions stored in the at least one memory of the system, when executed, further cause the one or more processors to:
establish a connection between the input device and the computing device; and
transmit an input from the input device to the computing device.

13. A therapeutic system, comprising:
a wearable device having an input device configured to monitor at least one exercise performed by a user; and
a computing device comprising:
one or more processors; and
at least one memory coupled to the one or more processors and storing program instructions that when executed by the one or more processors cause the one or more processors to:
provide a rehabilitation routine including the at least one exercise by generating a user interface displaying a content, the content comprising an exercise list and the exercise list comprising at least one exercise card corresponding to at least one exercise;
access a first exercise card in the exercise list in order to provide an instruction associated with a first exercise corresponding to the first exercise card;
determine, based on data from the wearable device, an indication of movement associated with the first exercise;
provide, based on the indication of movement, a real-time evaluation of the first exercise;
perform, based on the real-time evaluation of the first exercise, an operation; and
in response to a discontinuation of the rehabilitation routine according to the real-time evaluation of the first exercise, disable access to the first exercise card in the exercise list within a predetermined time.

14. The therapeutic system of claim 13, wherein the input device comprises a sensor chip for providing a measurement data as an input for the determination of the indication of movement.

15. The therapeutic system of claim 13, wherein the operation comprises generating a visual effect to indicate a progress made toward an exercise goal.

16. The therapeutic system of claim 13, wherein the rehabilitation routine comprises one or more instruction data associated with the at least one exercise.

17. The therapeutic system of claim 16, further comprising:
an intelligence engine configured to:
perform an analysis of a condition of the user;
generate, based on the analysis, an arrangement of the one or more instruction data;
generate the rehabilitation routine for the user as a preset rehabilitation routine, the preset rehabilitation routine comprising the arrangement of the one or more instruction data; and
output the preset rehabilitation routine.

18. A method for determining an assessment of at least one exercise performed by a user, the method comprising:
monitoring the at least one exercise by an input device affixed to a wearable equipment on the user;
generating a user interface displaying a content by a computing device, the content comprising an exercise list and the exercise list comprising at least one exercise card;
accessing a first exercise card in the exercise list in order to provide an instruction associated with a first exercise corresponding to the first exercise card by the computing device;
determining, based on data from the wearable equipment, an indication of movement associated with the first exercise by the computing device;
determining, based on the indication of movement, an assessment of the first exercise;
performing, based on the assessment of the first exercise, an operation; and
in response to a discontinuation of the assessment of the first exercise, disabling access to the first exercise card in the exercise list within a predetermined time.

* * * * *